(12) United States Patent
Kavaldjiev et al.

(10) Patent No.: US 9,086,389 B2
(45) Date of Patent: Jul. 21, 2015

(54) SAMPLE INSPECTION SYSTEM DETECTOR

(71) Applicant: KLA-Tencor Corporation, Milpitas, CA (US)

(72) Inventors: Daniel Ivanov Kavaldjiev, San Jose, CA (US); Stephen Biellak, Sunnyvale, CA (US); Guoheng Zhao, Palo Alto, CA (US); Mehdi Vaez-Iravani, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 83 days.

(21) Appl. No.: 14/062,832

(22) Filed: Oct. 24, 2013

(65) Prior Publication Data

US 2014/0118730 A1 May 1, 2014

Related U.S. Application Data

(60) Provisional application No. 61/719,048, filed on Oct. 26, 2012.

(51) Int. Cl.
*G01N 21/00* (2006.01)
*G01N 21/95* (2006.01)
*H01L 27/144* (2006.01)

(52) U.S. Cl.
CPC ........ *G01N 21/9501* (2013.01); *H01L 27/1446* (2013.01)

(58) Field of Classification Search
CPC .................. G01N 21/9501; H01L 27/1446
USPC .......................................................... 356/237.5
See application file for complete search history.

(56) References Cited

U.S. PATENT DOCUMENTS

| | | |
|---|---|---|
| 6,608,676 B1 | 8/2003 | Zhao et al. |
| 2006/0250611 A1 | 11/2006 | Velidandla et al. |
| 2008/0203309 A1 | 8/2008 | Frach et al. |
| 2009/0290162 A1 | 11/2009 | Erkmen et al. |
| 2011/0240865 A1 | 10/2011 | Frach et al. |
| 2012/0043466 A1 | 2/2012 | Weidenbruch et al. |
| 2012/0156714 A1 | 6/2012 | O'Brien et al. |
| 2013/0258093 A1 | 10/2013 | Jingu |
| 2013/0321798 A1 * | 12/2013 | Urano et al. ............ 356/237.5 |

* cited by examiner

*Primary Examiner* — Roy M Punnoose
(74) *Attorney, Agent, or Firm* — Spano Law Group; Joseph S. Spano

(57) ABSTRACT

Methods and systems for enhancing the dynamic range of a high sensitivity inspection system are presented. The dynamic range of a high sensitivity inspection system is increased by directing a portion of the light collected from each pixel of the wafer inspection area toward an array of avalanche photodiodes (APDs) operating in Geiger mode and directing another portion of the light collected from each pixel of the wafer inspection area toward another array of photodetectors having a larger range. The array of APDs operating in Geiger mode is useful for inspection of surfaces that generate extremely low photon counts, while other photodetectors are useful for inspection of larger defects that generate larger numbers of scattered photons. In some embodiments, the detected optical field is split between two different detectors. In some other embodiments, a single detector includes both APDs operating in Geiger mode and other photodetectors having a larger range.

20 Claims, 7 Drawing Sheets

SAMPLE INSPECTION SYSTEM DETECTOR

CROSS REFERENCE TO RELATED APPLICATION

The present application for patent claims priority under 35 U.S.C. §119 from U.S. provisional patent application Ser. No. 61/719,048, entitled "Sample Inspection System," filed Oct. 26, 2012, the subject matter of which is incorporated herein by reference.

TECHNICAL FIELD

The described embodiments relate to systems for surface inspection, and more particularly to semiconductor wafer inspection modalities.

BACKGROUND INFORMATION

Semiconductor devices such as logic and memory devices are typically fabricated by a sequence of processing steps applied to a substrate or wafer. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Inspection processes are used at various steps during a semiconductor manufacturing process to detect defects on wafers to promote higher yield. As design rules and process windows continue to shrink in size, inspection systems are required to capture a wider range of physical defects on wafer surfaces while maintaining high throughput.

One such inspection system is a scanning inspection system that illuminates and inspects a wafer surface. Light collected from the wafer surface is directed to a detector, or an array of detectors, for conversion to electrical signals useful for storage and analysis. Typical detector arrays are limited in their sensitivity due to significant detector noise. Often, this results in inspection systems that operate in a detector noise limited regime, rather than a photon limited, or surface limited regime. In some examples, detector noise is overcome by increasing the amount of illumination power. However, in high-power, laser-based inspection systems, increasing the power density of the incident laser beam may cause damage to the wafer surface. In addition, increasing the illumination power, particularly at short wavelengths, increases cost and may introduce reliability risks.

Previous inspection systems have relied on a variety of detectors, each with different advantages and disadvantages in specific applications. Exemplary detectors include photomultiplier tubes (PMTs), charge-coupled devices (CCDs), PIN diodes, photodiodes, etc. Each of these detectors presents its own challenges and shortcomings. PMTs, for example, are typically bulky, and require high drive voltage. PMTs are also not available in large arrays. CCDs suffer from internal readout noise mechanisms that limit their ultimate sensitivity compared with PMTs.

Avalanche photodiodes (APDs) are small sensors that provide significant gain and require lower drive voltage than PMTs. APDs may be configured in one of two operational modes. In linear mode, the voltage across the APD is set at a value below the break-down voltage. The output of the APD in this mode is a signal that is proportional to the amount of light detected. The gain of the APD may be set at relatively low values (e.g. 100×). In Geiger mode, the voltage across the APD is set at a value above the break-down voltage. In this mode, the gain of the APD becomes very large. Absorption of a single photon may give rise to a large pulse at the output that may be passed through a comparator to generate a clean TTL-like pulse. Thus, very high sensitivity may be achieved by APDs operating in Geiger mode.

However, once a Geiger pulse is trigged the APD is not responsive (i.e., "blind") to the arrival of another photon until a period of time (i.e., the "quench time" associated with the APD) has passed. Once the APD pulse is "quenched", the APD is again able to detect another photon. A typical quench time associated with an APD operating in Geiger mode is a few hundred picoseconds. Unfortunately, this period of blindness limits the dynamic range of APDs operating in Geiger mode, and thus limits their utility in current wafer inspection systems.

Improvements to the sensitivity and dynamic range of array based detectors employed in surface inspection systems are desired to detect defects on a wafer surface with greater sensitivity while avoiding thermal damage to the wafer surface.

SUMMARY

Methods and systems for enhancing the dynamic range of a high sensitivity inspection system are presented.

In one aspect, the dynamic range of the inspection system is increased by directing a portion of the light collected from each pixel of the wafer inspection area toward an array of avalanche photodiodes operating in Geiger mode and directing another portion of the light collected from each pixel of the wafer inspection area toward another array of photodetectors (e.g., an array of avalanche photodiodes operating in linear mode, PIN photodiodes, PMTs, CCDs, etc.). The array of avalanche photodiodes operating in Geiger mode is useful for inspection of surfaces that generate extremely low photon counts. The other array of photodetectors is useful for inspection of larger defects that generate larger numbers of scattered photons. The array of avalanche photodiodes operating in Geiger mode has a different resolution than the other array of photodetectors to optimize the dynamic range of the overall detector system.

In one embodiment, light scattered from each pixel of the inspection area of the surface of a wafer is collected and directed to a beam splitter. The beam splitter directs a portion of the collected light to an array detector that includes a number of avalanche photodiodes (APDs) operating in a Geiger mode. Similarly, the beam splitter directs another portion of the collected light to another array of photodetectors. Both detectors generate output signals usable in combination to determine the presence of anomalies and their characteristics with high sensitivity and large dynamic range.

In another embodiment, light scattered from each pixel of the inspection area of the surface of a wafer is collected and directed to an array detector that includes a number of avalanche photodiodes (APDs) operating in a Geiger mode. A portion of collected light is absorbed by the array detector. Another portion of the collected light is reflected from the surface of the array detector and is directed toward another array of photodetectors. Both detectors generate output signals usable in combination to determine the presence of anomalies and their characteristics with high sensitivity and large dynamic range.

In yet another embodiment, light scattered from each pixel of the inspection area of the surface of a wafer is collected and directed to an array detector configured in a stacked layer arrangement. Incoming light passes through a first array of photodetectors disposed in a first layer at the top surface of detector and a second array of photodetectors are disposed in a second layer of detector 160, below the first layer. The first array of photodetectors includes a number of avalanche photodiodes (APDs) operating in a Geiger mode.

In another aspect, an array detector may include other photodetectors in addition to APDs operating in a Geiger mode.

In one embodiment a detector includes a linear array of macro-pixels. Each macro-pixel includes a number of APDs operating in Geiger mode and connected in parallel such that multiple photons arriving simultaneously are properly counted. In addition each macro-pixel includes a number of APDs operating in a linear mode. Moreover, each macro pixel may be configured to generate separate output signals; one indicative of the number of photons counted by the APDs operating in Geiger mode, and another indicative of the radiation flux detected by the APDs operating in a linear mode. In some embodiments, light collected from each pixel of an inspection area on the wafer surface is imaged onto a macro-pixel. Hence, a portion of light collected from each pixel of an inspection area of the wafer surface is detected by one or more APDs operating in a Geiger mode and another portion of light collected from the same pixel is detected by another photodetector within the same integrated detector.

In another embodiment a detector includes a linear array of APDs operating in Geiger mode disposed adjacent to another linear array of photodetectors (e.g., APDs operating in linear mode). In some embodiments, light collected from each pixel of an inspection area on the wafer surface is imaged onto adjacent pixels of both linear arrays. Hence, a portion of light collected from each pixel of an inspection area of the wafer surface is detected by one or more APDs operating in a Geiger mode and another portion of light collected from the same pixel is detected by another photodetector within the same integrated detector.

In yet another embodiment a detector includes a linear array of APDs operating in Geiger mode interleaved with another linear array of photodetectors (e.g., APDs operating in linear mode). In some embodiments, light collected from each pixel of an inspection area on the wafer surface is imaged onto adjacent pixels of both linear arrays. Hence, a portion of light collected from each pixel of an inspection area of the wafer surface is detected by one or more APDs operating in a Geiger mode and another portion of light collected from the same pixel is detected by another photodetector within the same integrated detector.

In another aspect, the APDs of a detector array are configured to be switchable between a Geiger mode and a linear mode of operation. In one embodiment, a linear array detector includes drive electronics configured to switch APD elements between a Geiger mode of operation and a linear mode of operation in response to a control signal.

In some embodiments, a number of APDs are switched between a Geiger mode of operation and a linear mode of operation at a particular switching frequency and duration (e.g., pulse width modulated signal). Based on output signals received from the detector array, either or both of the switching frequency and duration values may be adjusted to emphasize or deemphasize output data generated by APDs operating in a Geiger mode.

In some other embodiments, a number of APDs are switched between a Geiger mode of operation and a linear mode of operation based on the saturation level of APDs operating in Geiger mode.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Figure 1:
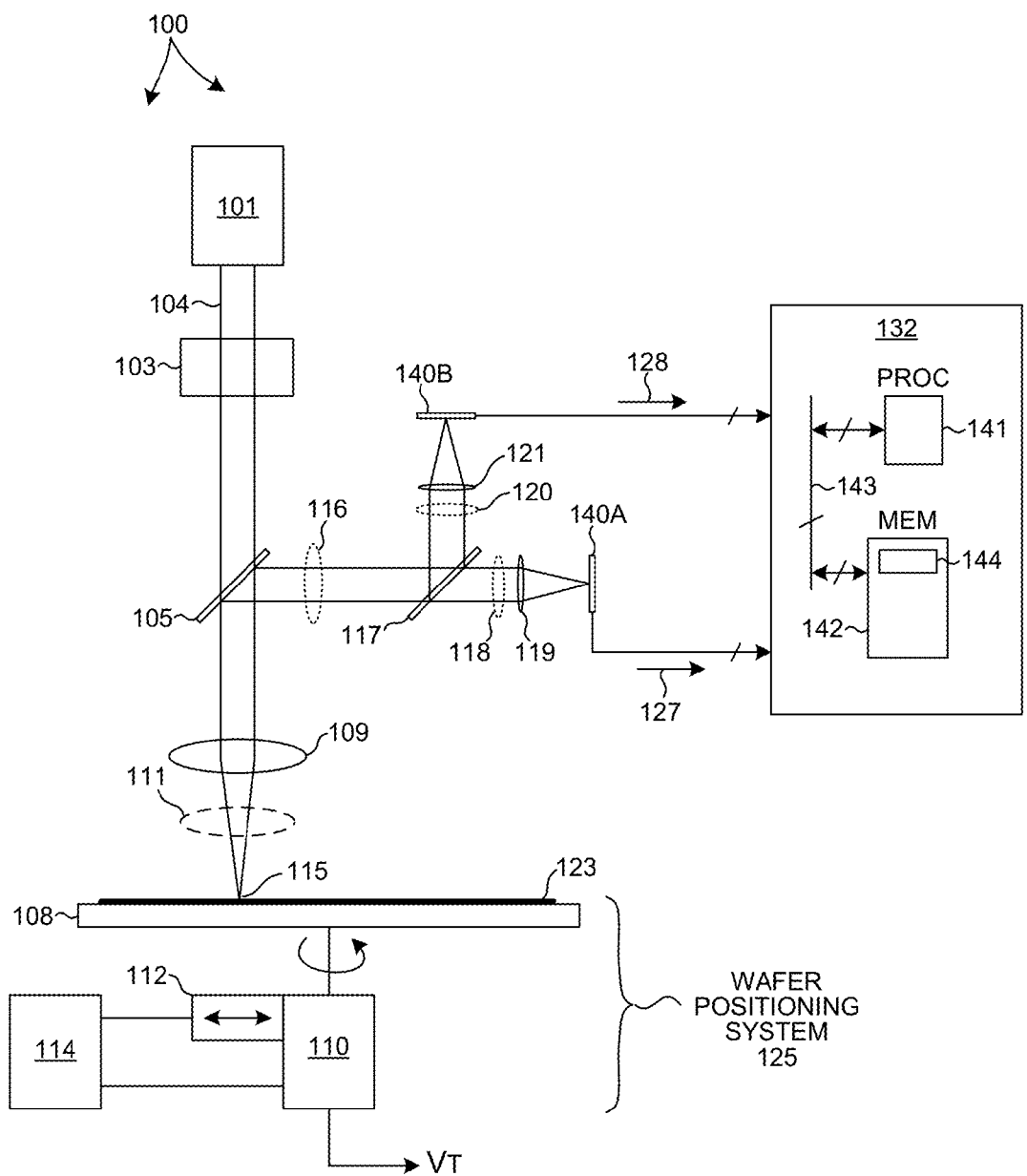
FIG. 1 is a simplified diagram illustrative of one embodiment of an inspection system 100 including a first array of photodetectors including a number of avalanche photodiodes (APDs) operable in a Geiger mode and a second array of photodetectors.

FIG. 1 is a simplified schematic view of one embodiment of a surface scanning inspection system 100 that may be used to perform the inspection methods described herein. For simplification, some optical components of the system have been omitted. By way of example, folding mirrors, polarizers, beam forming optics, additional light sources, additional collectors, and additional detectors may also be included. All such variations are within the scope of the invention described herein. The inspection system described herein may be used for inspecting patterned, as well as unpatterned wafers.

As illustrated in FIG. 1, a wafer 123 is illuminated by a normal incidence beam 111 generated by one or more illumination sources 101. Alternatively, the illumination subsystem may be configured to direct the beam of light to the specimen at an oblique angle of incidence. In some embodiments, system 100 may be configured to direct multiple beams of light to the specimen such as an oblique incidence beam of light and a normal incidence beam of light. The multiple beams of light may be directed to the specimen substantially simultaneously or sequentially.

Illumination source 101 may include, by way of example, a laser, a diode laser, a helium neon laser, an argon laser, a solid state laser, a diode pumped solid state (DPSS) laser, a xenon arc lamp, a gas discharging lamp, and LED array, or an incandescent lamp. The light source may be configured to emit near monochromatic light or broadband light. In general, the illumination subsystem is configured to direct light having a relatively narrow wavelength band to the specimen (e.g., nearly monochromatic light or light having a wavelength range of less than about 20 nm, less than about 10 nm, less than about 5 nm, or even less than about 2 nm). Therefore, if the light source is a broadband light source, the illumination subsystem may also include one or more spectral filters that may limit the wavelength of the light directed to the specimen. The one or more spectral filters may be bandpass filters and/or edge filters and/or notch filters.

In the embodiment depicted in FIG. 1, system 100 includes a beam shaping element 103 that reshapes the beam intensity distribution of illumination light 104 to generate a reshaped beam of illumination light 111 that is projected on the surface of wafer 123. Illumination light 111 is directed to the wafer surface and is incident to the surface of wafer 123 over an illumination spot 115. In one embodiment, beam shaping element 103 includes a diffractive optical element to generate the desired beam shape. In other embodiments, beam shaping element 103 includes an optical beam shaper to generate the desired beam shape. In other embodiments, beam shaping element 103 includes an apodizer to generate the desired intensity profile. However, due to the attenuation of illumination power associated with apodizers, it is preferable to limit the use of apodizers to inspection modes that are not starved for illumination power. In another embodiment, beam shaping element 103 is a cylindrical lens positioned parallel to the wafer surface as described in U.S. Pat. No. 6,608,676, entitled "System for Detecting Anomalies And/Or Features of a Surface," issued on Aug. 19, 2003, and assigned to KLA-Tencor Corporation, the subject matter of which is incorporated herein by reference in its entirety.

In the embodiment depicted in FIG. 1, a beam splitter 105 directs the reshaped illumination light to an objective lens 109. Objective lens 109 focuses the reshaped illumination light 111 onto a wafer 123 at illumination spot 115. In this manner, illumination spot 115 is shaped and sized by the projection of light emitted from beam shaping element 103 onto the surface of wafer 123.

In some embodiments, reflected/scattered light is collected and detected from all of the area of illumination spot 115 over a particular sample period by inspection system 100. In this manner, as much light as possible is collected by inspection system 100. However, in some other embodiments, reflected/scattered light is collected and detected from a portion of the area of illumination spot 115 over a particular sample period by inspection system 100.

Optical elements in a collection path of inspection system 100 collect light scattered and/or reflected from the surface of wafer 123 over each pixel of an inspection area on the wafer surface and focus the collected light onto one or more elements of a detector subsystem.

In one aspect, the dynamic range of the detector subsystem is increased by directing a portion of the light collected from each pixel of the wafer inspection area toward an array of avalanche photodiodes operating in Geiger mode and directing another portion of the light collected from each pixel of the wafer inspection area toward another array of photodetectors (e.g., an array of avalanche photodiodes operating in linear mode, PIN photodiodes, PMTs, CCDs, etc.). The array of avalanche photodiodes operating in Geiger mode is useful for inspection of surfaces that generate extremely low photon counts. The other array of photodetectors is useful for inspection of larger defects that generate plenty of scattered photons.

In the embodiment illustrated in FIG. 1, light scattered from each pixel of the inspection area of the surface of wafer 123 is collected by objective lens 109. This light passes back through objective lens 109 and impinges on beam splitter 105. Beam splitter 105 directs collected light 116 toward beam splitter 117. Beam splitter 117 directs a portion 118 of collected light 116 to imaging lens 119, which in turn focuses the portion 118 of collected light 116 onto detector 140A. Detector 140A includes a number of APDs operating in a Geiger mode. Similarly, beam splitter 117 directs a portion 120 of collected light 116 to imaging lens 121, which in turn focuses the portion 120 of collected light 116 onto detector 140B. Beam splitter 117 is configured to apportion collected light 116 between detector 140A and 140B. The portions 118 and 120 of collected light 116 may be equal or unequal. For example, in some embodiments, beam splitter may be configured to direct a larger portion of collected light 116 toward detector 140A, while in other embodiments; beam splitter 117 may be configured to direct a larger portion of collected light 116 toward detector 140B. As depicted in FIG. 1, an output signal 127 generated by detector subsystem 140A and an output signal 128 generated by detector subsystem 140B are supplied to a computer 132 for signal processing to determine the presence of anomalies and their characteristics.

Figure 2:
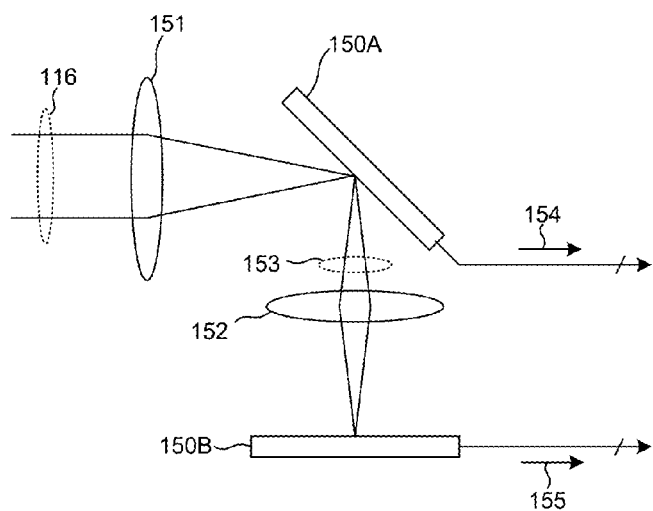
FIG. 2 is a simplified diagram illustrative of a first array of photodetectors including a number of avalanche photodiodes (APDs) operable in a Geiger mode and a second array of photodetectors in another embodiment.

In another embodiment, illustrated in FIG. 2, collected light 116 is imaged onto detector 150A by imaging lens 151. A portion of collected light 116 is absorbed by detector 150A which includes a number of APDs operating in Geiger mode. Another portion 153 of collected light 116 is reflected from the surface of detector 150A and is imaged onto detector 150B. As depicted in FIG. 2, an output signal 154 generated by detector subsystem 150A and an output signal 155 generated by detector subsystem 150B are supplied to a computer (e.g. computer 132) for signal processing to determine the presence of anomalies and their characteristics. As illustrated in FIG. 2, the portion of collected light reflected from detector 150A is directed to detector 150B, and is either absorbed by photodetectors of detector 150B, or lost. However, in other embodiments, detector 150B may be configured to reflect a portion of incoming light 153 toward yet another detector, and so on. Thus, in general, the cascading arrangement of detectors illustrated in FIG. 2 may be extended to any number of detectors.

Figure 3:
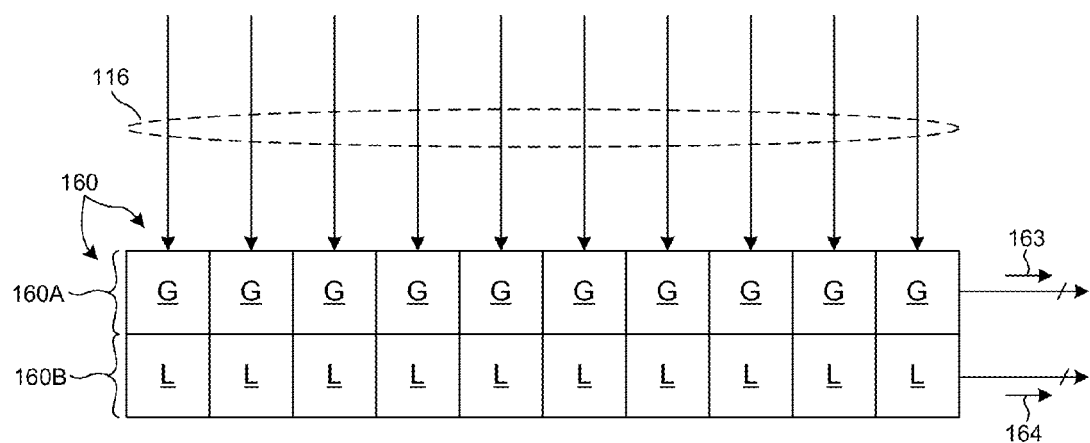
FIG. 3 is a simplified diagram illustrative of a first array of photodetectors including a number of avalanche photodiodes (APDs) operable in a Geiger mode and a second array of photodetectors in yet another embodiment.

In yet another embodiment, illustrated in FIG. 3, collected light 116 is imaged onto detector 160. Detector 160 is configured in a stacked layer arrangement where incoming light passes through a first array of photodetectors 160A disposed in a first layer at the top surface of detector 160 and a second array of photodetectors 160B are disposed in a second layer of detector 160, below the first layer. This detector arrangement is sometimes referred to as a "three dimensional detector" because the active area of the detector not only extends in two dimensions across the surface of the detector, but also extends in a third dimension below the surface of the detector.

As depicted in FIG. 3, the first array of photodetectors 160A includes APDs operating in Geiger mode. Output signal 163 is generated by detector 160A. In addition, the second array of photodetectors 160B includes additional photodetectors (e.g., APDs operating in a linear mode). Output signal 164 is generated by detector subsystem 160B. Output signals 163 and 164 are supplied to a computer 132 for signal processing to determine the presence of anomalies and their characteristics.

In the embodiment depicted in FIG. 1, detector subsystem 140 generates bright field signals. However, in general, inspection system 100 may employ various imaging modes, such as bright field, dark field, and confocal. As depicted in FIG. 1, imaging lens 119 and imaging lens 120 image light collected by objective lens 109 onto detector arrays 140B and 140A, respectively. However, in addition, an aperture or Fourier filter, which can rotate in synchronism with the wafer, may be placed at the back focal plane of objective lens 109. Various imaging modes such as bright field, dark field, and phase contrast can be implemented by using different apertures or Fourier filters. U.S. Pat. Nos. 7,295,303 and 7,130,039, which are incorporated by reference herein, describe these imaging modes in further detail. In another example (not shown), a detector generates dark field images by imaging scattered light collected at larger field angles. In another example, a pinhole that matches the illumination spot 115 can be placed in front of a detector (e.g., detector 140) to generate a confocal image. U.S. Pat. No. 6,208,411, which is incorporated by reference herein, describes these imaging modes in further detail. In addition, various aspects of surface inspection system 100 are described in U.S. Pat. Nos. 6,271,916 and 6,201,601, both of which are incorporated herein by reference.

In general, optical elements in the collection path of inspection system 100 may include a lens, a compound lens, or any appropriate lens known in the art. Alternatively, any optical element in the collection path may be reflective or partially reflective, such as a mirror. In addition, although particular collection angles are illustrated in FIG. 1, it is to be understood that the collection optics may be arranged at any appropriate collection angle. The collection angle may vary depending upon, for example, the angle of incidence and/or topographical characteristics of the specimen.

As described hereinbefore with reference to the embodiments depicted in FIGS. 1-3, detectors 140A, 150A, and 160A, respectively, include a number of APDs operating in a Geiger mode. In some embodiments, detectors 140A, 150A, and 160A may include only APDs operating in a Geiger mode. However, in some other embodiments, detectors 140A, 150A, and 160A may also include other photodetectors in addition to the APDs operating in a Geiger mode.

Figure 4:
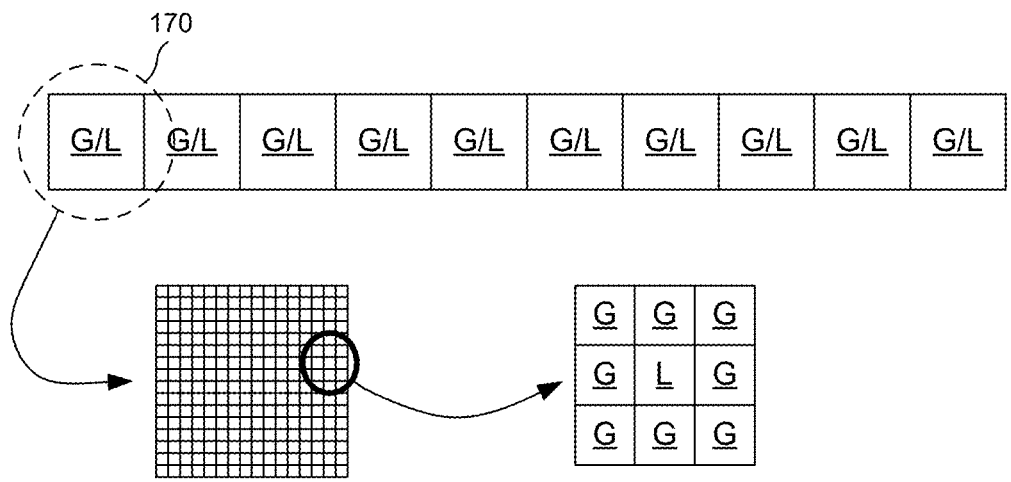
FIG. 4 is a simplified diagram illustrative of a detector employing both APDs operable in a Geiger mode and other photodetectors in one embodiment.

In one embodiment depicted in FIG. 4, detectors 140A, 150A, and 160A include a linear array of macro-pixels (e.g., macro-pixel 170). Each macro-pixel 170 includes a number of APDs operating in Geiger mode and connected in parallel such that multiple photons arriving simultaneously are properly counted. In addition each macro-pixel includes a number of APDs operating in a linear mode. Moreover, each macro pixel may be configured to generate separate output signals; one indicative of the number of photons counted by the APDs operating in Geiger mode, and another indicative of the radiation flux detected by the APDs operating in a linear mode. In some embodiments, light collected from each pixel of an inspection area on the wafer surface is imaged onto a macro-pixel. Hence, a portion of light collected from each pixel of an inspection area of the wafer surface is detected by one or more APDs operating in a Geiger mode and another portion of light collected from the same pixel is detected by another photodetector within the same integrated detector.

Figure 5:
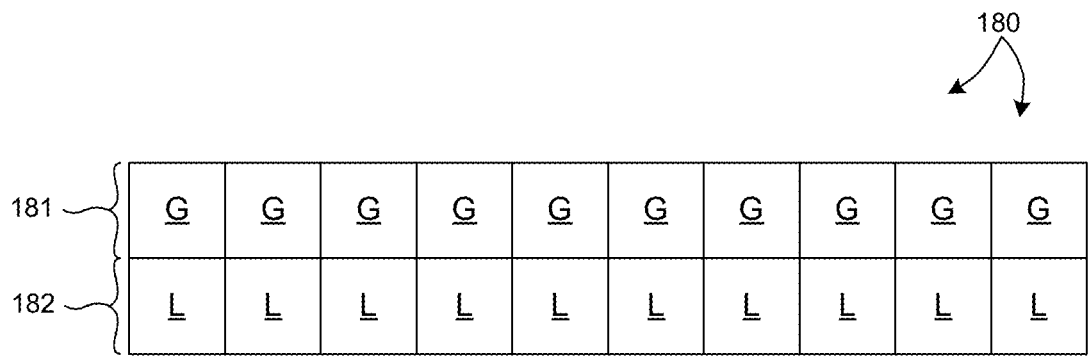
FIG. 5 is a simplified diagram illustrative of a detector employing both APDs operable in a Geiger mode and other photodetectors in another embodiment.

In another embodiment depicted in FIG. 5, detectors 140A, 150A, and 160A are configured similar to detector 180. Detector 180 includes a linear array 181 of APDs operating in Geiger mode and another linear array 182 of photodetectors (e.g., APDs operating in linear mode) disposed adjacent to linear array 181. In some embodiments, light collected from each pixel of an inspection area on the wafer surface is imaged onto adjacent pixels of both linear array 181 and linear array 182. Hence, a portion of light collected from each pixel of an inspection area of the wafer surface is detected by one or more APDs operating in a Geiger mode and another portion of light collected from the same pixel is detected by another photodetector within the same integrated detector.

Figure 6:
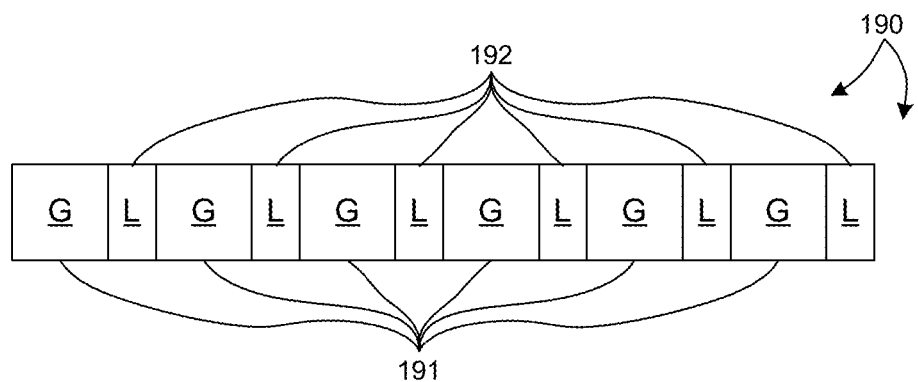
FIG. 6 is a simplified diagram illustrative of a detector employing both APDs operable in a Geiger mode and other photodetectors in yet another embodiment.

In another embodiment depicted in FIG. 6, detectors 140A, 150A, and 160A are configured similar to detector 190. Detector 190 includes a linear array 191 of APDs operating in Geiger mode interleaved with another linear array 192 of photodetectors (e.g., APDs operating in linear mode). In some embodiments, light collected from each pixel of an inspection area on the wafer surface is imaged onto adjacent pixels of both linear array 191 and linear array 192. Hence, a portion of light collected from each pixel of an inspection area of the wafer surface is detected by one or more APDs operating in a Geiger mode and another portion of light collected from the same pixel is detected by another photodetector within the same integrated detector.

As described hereinbefore with reference to the embodiments depicted in FIGS. 1-3, detectors 140B, 150B, and 160B, respectively, include a number of photodetectors. In some embodiments, detectors 140B, 150B, and 160B do not include APDs operating in a Geiger mode, but may include substantially any other photodetector known in the art. A particular detector may be selected for use within one or more embodiments of the invention based on desired performance characteristics of the detector, the type of specimen to be inspected, and the configuration of the illumination. For example, if the amount of light available for inspection is relatively low, an efficiency enhancing detector such as a time delay integration (TDI) camera may increase the signal-to-noise ratio and throughput of the system. However, other detectors such as charge-coupled device (CCD) cameras, PIN photodiodes, APDs operating in a linear mode, phototubes and photomultiplier tubes (PMTs) may be used, depending on the amount of light available for inspection and the type of inspection being performed.

However, in some other embodiments, detectors 140B, 150B, and 160B include APDs operating in a Geiger mode in addition to another type of photodetector. By way of non-limiting example, detectors 140B, 150B, and 160B are configured to the embodiments described with reference to FIGS. 4-6.

The proportion of APDs operating in Geiger mode in any of detectors 140A, 140B, 150A, 150B, 160A, and 160B relative to other photodetectors may be determined by expected operating conditions of the inspection system 100. For example, if the photon count is expected to be relatively small, more APDs operating in Geiger mode may be included relative to other photodetectors. Conversely, if the photon count is expected to be relatively large, fewer APDs operating in Geiger mode may be included relative to other photodetectors. In general, the interplay among photon count, light scattering by small defects, quench time of the detectors, and illumination pulse-length (where a pulsed illumination source is used), determines the design of an APD array in Geiger mode with enhanced dynamic range.

For example, in some embodiments, a Q-switched (pulsed) laser is employed. Q-switched lasers are able to deliver high illumination power to the target, thus increasing defect detection sensitivity. The pulse length in a Q-switched laser is typically of the order of 10's of nanoseconds at a repetition rate between a few hundred and 10,000 Hz. Lasers operating in this range are useful in two dimensional inspection applications.

Each pulse of a Q-switched laser may emit up to $10^{14}$ photons illuminating $10^5$-$10^6$ pixels of the sample surface. The scattering induced by extremely small defects on the surface of smooth unpatterned samples may be on the order of $10^{-6}$. Hence, for a small defect, perhaps, 100-1000 photons may arrive at each "macro-pixel" of the detector array. If the quench time of each APD operating in Geiger mode is 300 picoseconds, at most, one hundred photons could be detected by each APD operating in Geiger mode during the 30 nanosecond pulse of the laser. Hence in this example, a few APDs operating in parallel in a Geiger mode in each macro-pixel may provide sufficient dynamic range. For larger numbers of photons, or longer quench times, more APDs operating in parallel in a Geiger mode are required to maintain peak sensitivity.

Figure 7:
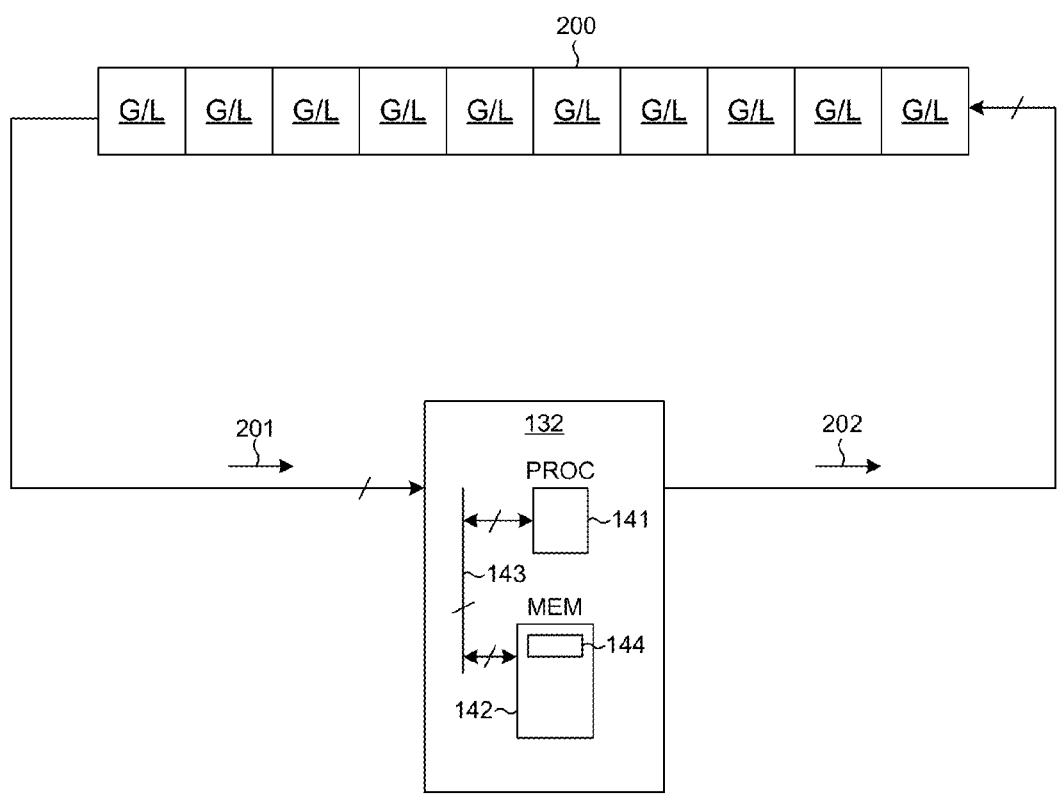
FIG. 7 is a simplified diagram illustrative of a detector including APDs that are switchable between a Geiger mode and a linear mode of operation.

In some embodiments, the number of APDs configured to operate in Geiger mode is fixed for a particular detector. However, in some other embodiments, any of detectors 140A, 140B, 150A, 150B, 160A, and 160B may be configured to adjust the number of APDs configured to operate in Geiger mode. FIG. 7 illustrates a linear array detector 200 including drive electronics (not shown) configured to switch APD elements of array 200 between a Geiger mode of operation and a linear mode of operation in response to a control command 202 from computer 132. Exemplary techniques for switching APDs between Geiger and linear mode are described in U.S. Patent Publication No. 2011/0240865 A1, entitled "High Dynamic Range Light Sensor," by Thomas Frach, et al. and published on Oct. 6, 2011, the subject matter of which is incorporated herein by reference in its entirety. In some embodiments, computer 132 switches a number of APDs between a Geiger mode of operation and a linear mode of operation at a particular switching frequency and duration (e.g., pulse width modulated signal). Based on output signals 201 received from detector 200, either or both of the switching frequency and duration values may be adjusted to emphasize or deemphasize output data generated by APDs operating in a Geiger mode. This can be achieved, for example, by applying a voltage modulation to the APD array such that the detectors are driven back and forth between the linear and Geiger regimes. In some other embodiments, computer 132 determines the saturation level of APDs operating in Geiger mode based on output signals 201 and determines control command 202 to adjust the number of APDs operating in Geiger mode, accordingly.

As depicted in FIG. 7, inspection system 100 includes a processor 141 and an amount of computer readable memory 142. Processor 141 and memory 142 may communicate over bus 143. Memory 142 includes an amount of memory 144 that stores a program code that, when executed by processor 141, causes processor 141 to determine the desired operational mode of each detector and generate a control signal that causes the detector to adjust the number of APDs operating in Geiger mode.

In one further aspect, a microlens array is disposed in front of the array of photodetectors to focus incoming light collected from each pixel of the inspection area onto the respective active areas of the array of photodetectors. In this manner, losses associated with incoming light incident on "dead space" between adjacent photodetectors of the array is minimized.

Figure 9A:
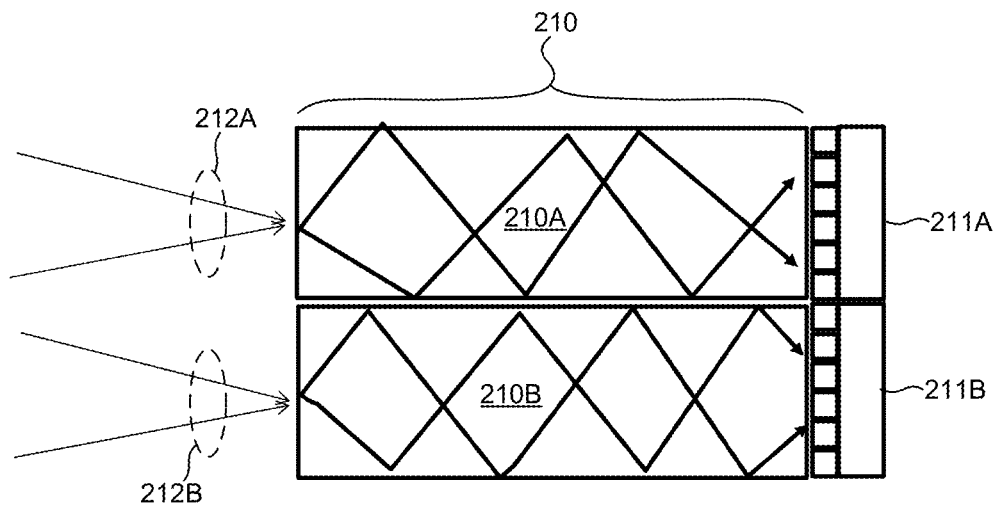
FIG. 9A is a diagram illustrative of a light pipe array 210 having light pipe elements 210A and 210B disposed in front of macro-pixels 211A and 211B, respectively.
Figure 9B:
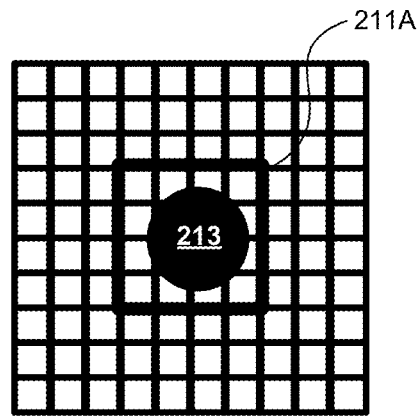
FIG. 9B is a diagram illustrative of a distribution 213 of incoming light 212A projected onto macro-pixel 211A depicted in FIG. 9A without mixing.
Figure 9C:
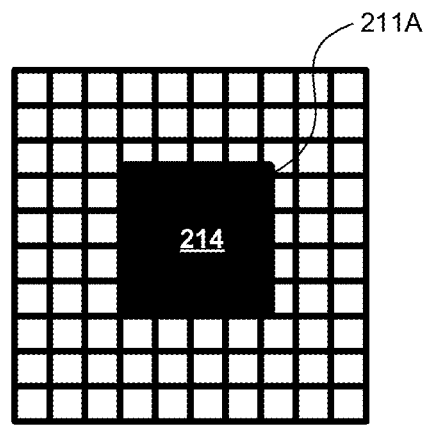
FIG. 9C is a diagram illustrative of a distribution 214 of incoming light 212A projected onto macro-pixel 211A with mixing by light pipe 210A depicted in FIG. 9A.

In another further aspect, a light pipe array is disposed in front of the array of photodetectors to evenly distribute light collected from each pixel of the inspection area onto each corresponding photodetector pixel. FIG. 9A illustrates a light pipe array 210 having light pipe elements 210A and 210B disposed in front of macro-pixels 211A and 211B, respectively. Macro-pixels 211A and 211B include a number of APDs operating in Geiger mode. Each of the APD elements (i.e., sub-pixels) that comprise the macro-pixel are connected in parallel such that multiple photons arriving simultaneously are properly counted. To maximize the dynamic range of each macro-pixel, light pipe array 210 evenly distributes incoming light corresponding to each macro-pixel over the active elements (e.g., APDs operating in Geiger mode) of each macro-pixel. In this manner, the likelihood that certain sub-pixels become saturated and unable to properly count incoming photons is minimized. As depicted in FIG. 9A, incoming light 212A corresponds with a particular pixel of the inspection area. Light pipe element 210A receives and mixes the incoming light 212A. The mixed light is then presented to macro-pixel 211A as an even distribution of light over each sub-pixel of macro-pixel 211A. In this manner, macro-pixel 211A is able to count the number of photons collected a corresponding pixel of the inspection area with maximum dynamic range. Similarly, incoming light 212B corresponds with another particular pixel of the inspection area. Light pipe element 210B receives and mixes the incoming light 212B. The mixed light is then presented to macro-pixel 211B as an even distribution of light over each sub-pixel of macro-pixel 211B. FIG. 9B illustrates a distribution 213 of incoming light 212A projected onto macro-pixel 211A without mixing. As depicted in FIG. 9B, many of the sub-pixels of macro-pixel 211A are not utilized because photons associated with incoming light 211A are concentrated on relatively few sub-pixels. As a result, the sub-pixels subject to the concentrated distribution 213 of incoming light 211A are more easily saturated. Hence, the dynamic range of macro-pixel 211A is reduced. FIG. 9C illustrates a distribution 214 of incoming light 212A projected onto macro-pixel 211A with mixing by light pipe 210A. As depicted in FIG. 9C, all of the sub-pixels of macro-pixel 211A are utilized because photons associated with incoming light 211A are evenly distributed over all of the sub-pixels. As a result, particular sub-pixels subject to the even distribution 214 of incoming light 211A are less likely to saturate. Hence, the dynamic range of macro-pixel 211A is improved.

Figure 10:
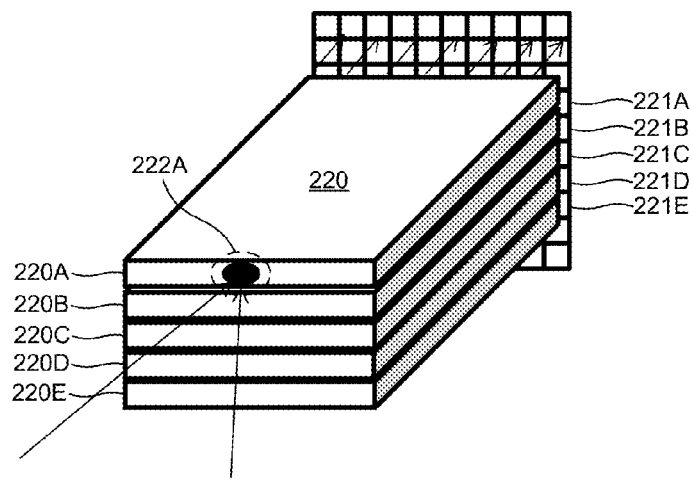
FIG. 10 is a diagram illustrative of a light pipe array 220 in another embodiment.

FIG. 10 is a diagram illustrative of a light pipe array 220 in another embodiment. As depicted in FIG. 10, light pipe array 220 includes light pipe elements 220A-220E disposed in front of macro-pixels 221A-221E, respectively. Each of macro-pixels 221A-221E includes a linear array of APDs operating in Geiger mode (i.e., sub-pixels). Each of the APD elements (i.e., sub-pixels) that comprise each macro-pixel are connected in parallel such that multiple photons arriving simultaneously are properly counted. To maximize the dynamic range of each macro-pixel, light pipe array 220 evenly distributes incoming light corresponding to each macro-pixel over the active elements (e.g., APDs operating in Geiger mode) of each macro-pixel. In this manner, the likelihood that certain sub-pixels become saturated and unable to properly count incoming photons is minimized. As depicted in FIG. 10, incoming light 222A corresponds with a particular pixel (e.g., linear stripe) of the inspection area. Light pipe element 220A receives and mixes the incoming light 222A. The mixed light is then presented to macro-pixel 221A as an even distribution of light over each sub-pixel of macro-pixel 221A. In this manner, macro-pixel 221A is able to count the number of photons collected a corresponding pixel of the inspection area with maximum dynamic range.

In another further aspect, the imaging resolution of the first array of photodetectors including APDs operating in Geiger mode (e.g., array 140A, 150A, or 160A) is different that the imaging resolution of the second array of photodetectors e.g., array 140B, 150B, or 160B). For example, the number of APDs coupled in parallel and operating in Geiger mode at each macro-pixel of a photodiode array determines the dynamic range of that particular photodiode array. As the number of APDs associated with each macro-pixel increases, so does the dynamic range. However, as the number of APDs increases, so does the size of the corresponding macro-pixel for an APD of fixed size. The increase in size of the macro-pixel results in reduced imaging resolution. Hence, a trade-off between imaging resolution and dynamic range of a particular macro-pixel exists based on the number of practically sized APD elements operating in Geiger mode. In a preferred embodiment, the photodetector array receiving more light is designed with a greater number of sub-pixels to increase dynamic range, while another photodetector array receiving less light includes a smaller number of sub-pixels to increase imaging resolution. In the preferred embodiment, one or more of the photodetector arrays includes APDs operating in Geiger mode.

Figure 11:
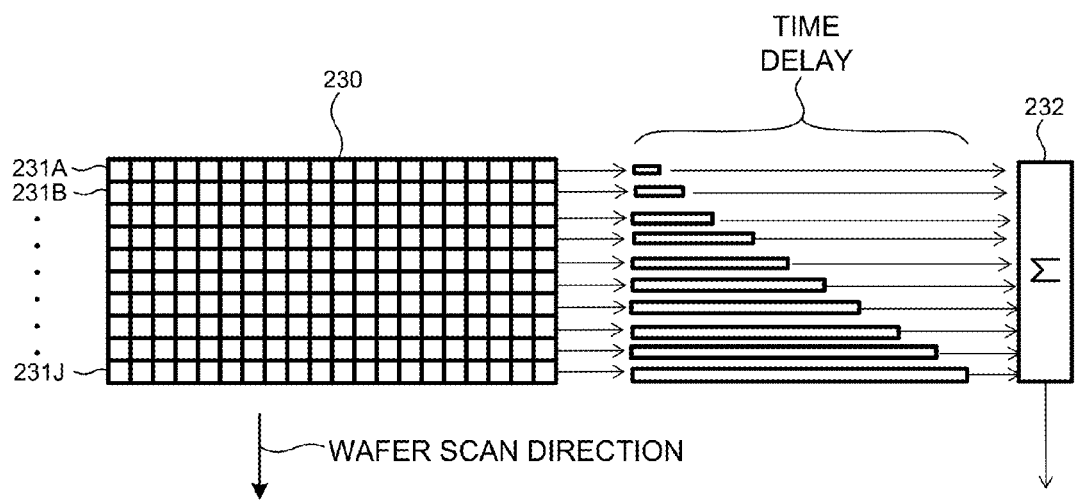
FIG. 11 is a diagram illustrative of a two dimensional array of photodetectors employed to perform one-dimensional measurements with increased dynamic range.

In yet another aspect, the dynamic range of a two dimensional array of photodetectors including APDs operating in a Geiger mode is increased without losing resolution. In the embodiment depicted in FIG. 11, a two dimensional array of photodetectors each including a number of APDs operating in Geiger mode is employed to perform one-dimensional measurements with increased dynamic range. As depicted in FIG. 11, two-dimensional array 230 includes a number of rows 231A-231J of photodetectors. A summation module 232, e.g., implemented by computer 132, reads out each row element separately, and sums each column of array 230 with a time delay corresponding to their columnar location. Since, the APDs of each photodetector of the array 230 are operating in a Geiger mode, the read out of each row element is a digital value (i.e., photon count value). Hence, the subsequent summation of the column elements is accurately performed without read-out noise. In this manner, a one-dimensional measurement is performed with the resolution determined by the size of the row elements, while the dynamic range is increased by the number of elements integrated in each column. The time delay associated with each column location is based on the scanning speed of the sample being inspected. For example, as the scanning speed of the sample is increased, the time delay is reduced. In some embodiments, the columnar elements are integrated over a straight line. However, in general, the columnar elements can be integrated over an arbitrary curved trajectory.

In some embodiments, drive and readout electronics are constructed on the same substrate as the APDs to reduce cost and improve data processing speed.

In some embodiments, APDs are front illuminated avalanche photodiodes. However, in some other embodiments, back-thinned avalanche photodiodes are employed. The use of back-thinned APDs may be preferred when sensitivity to short wavelength radiation (e.g., deep ultraviolet radiation) is desired.

In some embodiments, the pixel structure of the array is designed to maximize collection efficiency over a range of radiation wavelengths (e.g., DUV and fluorescence signals). In this manner, the array is sensitive to all radiation wavelengths within a prescribed range.

In some embodiments where excess illumination power is available, the central portion of the scattered illuminated field is imaged into a slit aperture. The light spreads out through the aperture and onto the detector array, thus enhancing sensitivity.

In some embodiments, the size of a relatively large particle is estimated based on the output signals generated by detector elements corresponding to the edges of a group of saturated detector elements. For example, a large particle may cause a saturation of signal in the central parts of the image of the defect (i.e., power spectral function of the collector lens) on the detector array. Output signals generated by detector elements on the fringes of the saturated detectors are used to estimate the size of the defect.

In some embodiments of a scanning surface inspection system, each detector generates a single output signal indicative of the light collected from an inspection area illuminated by illumination spot 115. A single output signal allows for efficient detection of defects with high throughput. In some other embodiments, imaging detectors (i.e., a detector(s) that generate a number of separate output signals indicative of light collected over each pixel of the inspection area illuminated by illumination spot 115) are employed.

System 100 also includes various electronic components (not shown) needed for processing the scattered signals detected by each detector. For example, system 100 may include amplifier circuitry to receive output signal 127 from detector 140A and output signal 128 from detector 140B and to amplify the output signals by a predetermined amount. In addition, an analog-to-digital converter (ADC) (not shown) is included to convert the amplified signals into a digital format suitable for use within processor 141. In one embodiment, the processor may be coupled directly to an ADC by a transmission medium. Alternatively, the processor may receive signals from other electronic components coupled to the ADC. In this manner, the processor may be indirectly coupled to the ADC by a transmission medium and any intervening electronic components.

In general, processor 141 is configured to detect features, defects, or light scattering properties of the wafer using electrical signals obtained from each detector. The signals produced by the detector are representative of the light detected by each detector. The processor may include any appropriate processor known in the art. In addition, the processor may be configured to use any appropriate defect detection algorithm or method known in the art. For example, the processor may use a die-to-database comparison or a thresholding algorithm to detect defects on the specimen.

In addition, inspection system 100 may include peripheral devices useful to accept inputs from an operator (e.g., keyboard, mouse, touchscreen, etc.) and display outputs to the operator (e.g., display monitor). Input commands from an operator may be used by processor 141 to adjust threshold values used to control illumination power. The resulting power levels may be graphically presented to an operator on a display monitor.

In the embodiment illustrated in FIG. 1, wafer positioning system 125 moves wafer 123 under a stationary beam of illumination light 111. Wafer positioning system 125 includes a wafer chuck 108, motion controller 114, a rotation stage 110 and a translation stage 112. Wafer 123 is supported on wafer chuck 108. Wafer 123 is located with its geometric center approximately aligned with the axis of rotation of rotation stage 110. In this manner, rotation stage 110 spins wafer 123 about its geometric center at a specified angular velocity, ω, within an acceptable tolerance. In addition, translation stage 112 translates the wafer 123 in a direction approximately perpendicular to the axis of rotation of rotation stage 110 at a specified velocity, VT. Motion controller 114 coordinates the spinning of wafer 123 by rotation stage 110 and the translation of wafer 123 by translation stage 112 to achieve the desired scanning motion of wafer 123 within scanning surface inspection system 100.

In some embodiments, system 100 may include a deflector (not shown). In one embodiment, the deflector may be an acousto-optical deflector (AOD). In other embodiments, the deflector may include a mechanical scanning assembly, an electronic scanner, a rotating mirror, a polygon based scanner, a resonant scanner, a piezoelectric scanner, a galvo mirror, or a galvanometer. The deflector scans the light beam over the specimen. In some embodiments, the deflector may scan the light beam over the specimen at an approximately constant scanning speed.

Although, the aforementioned detection schemes have been described with reference to an individual illumination spot (e.g., illumination spot 115), the methods and systems described herein may also be applied analogously to a multi-spot surface inspection system. In a multi-spot inspection system, a number of illumination spots are employed simultaneously. Illumination light is supplied to these illumination spots from one or more illumination sources. Detectors, such as those described herein, may be selectively placed in the collection path of light reflected/scattered from any of the multiple illumination spots. In this manner, defect sensitivity at any of the illumination spots may be improved. Typically, illumination spots are configured with considerable spacing between spots such that inspection results may be interleaved among successive portions of an inspection track and cross-talk at the detectors is minimized. U.S. Pat. Publication No. 2009/0225399, which is incorporated by reference herein, describes multi-spot scanning techniques in further detail.

Figure 8:
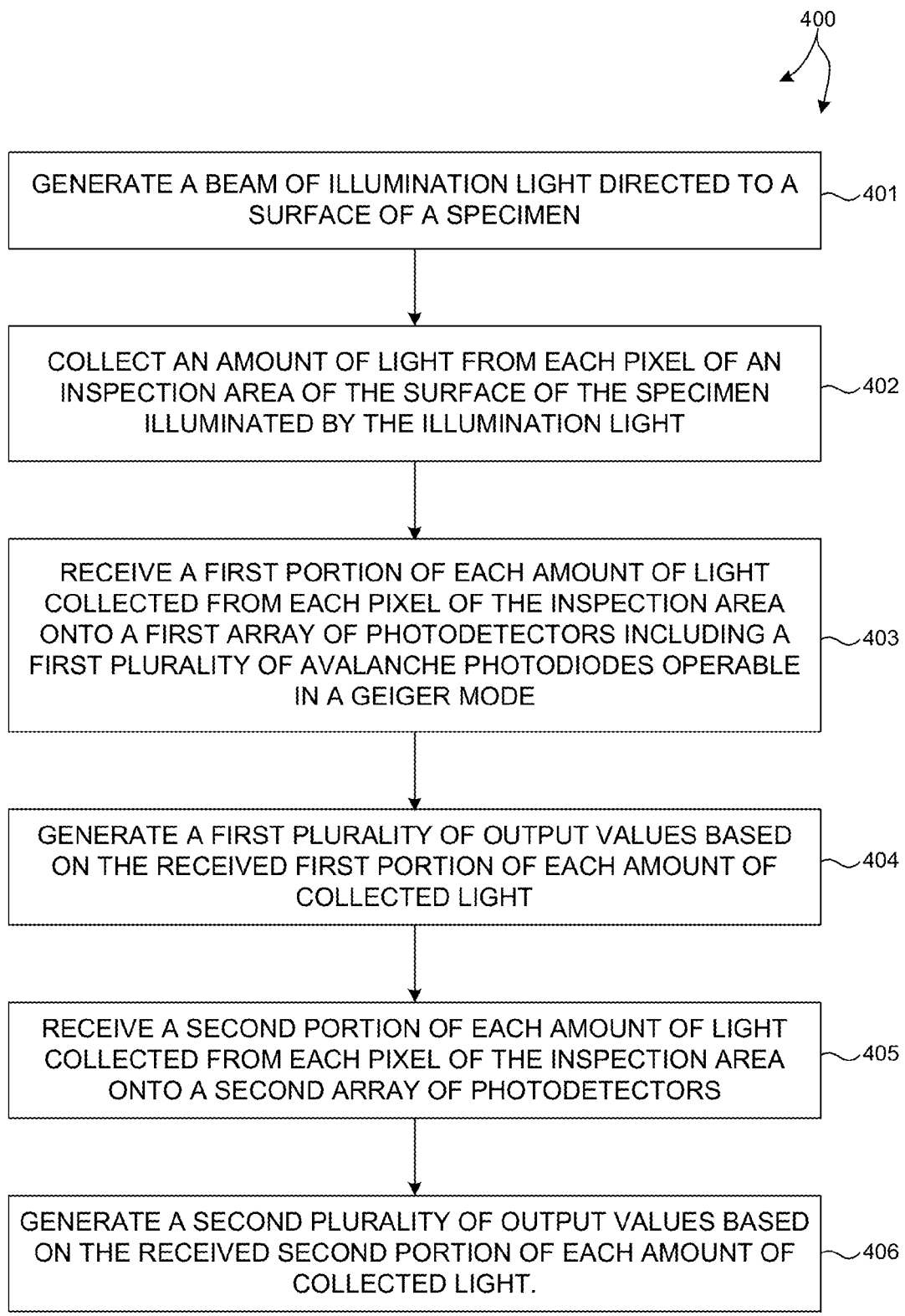
FIG. 8 is a flowchart illustrative of a method 400 of enhancing the dynamic range of a high sensitivity inspection system.

FIG. 8 illustrates a flowchart of an exemplary method 400 useful for enhancing the dynamic range of detection systems including APDs operable in a Geiger mode. In one non-limiting example, inspection system 100, described with reference to FIG. 1 is configured to implement method 400. However, in general, the implementation of method 400 is not limited by the specific embodiments described herein.

In block 401, a beam of illumination light is generated by an illumination source and directed to a surface of a specimen.

In block 402, an amount of light is collected from each pixel of an inspection area of the surface of the specimen illuminated by the illumination light.

In block 403, a first portion of each amount of light collected from each pixel of the inspection area is received onto a first array of photodetectors including a first plurality of avalanche photodiodes operable in a Geiger mode.

In block 404, a first plurality of output values are generated based on the received first portion of each amount of collected light.

In block 405, a second portion of each amount of light collected from each pixel of the inspection area is received onto a second array of photodetectors.

In block 406, a second plurality of output values is generated based on the received second portion of each amount of collected light.

Various embodiments are described herein for an inspection system or tool that may be used for inspecting a specimen. The term "specimen" is used herein to refer to a wafer, a reticle, or any other sample that may be inspected for defects, features, or other information (e.g., an amount of haze or film properties) known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media be any available media that can be accessed a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. In one example, inspection system 100 may include more than one light source (not shown). The light sources may be configured differently or the same. For example, the light sources may be configured to generate light having different characteristics that can be directed to a wafer at the same or different illumination areas at the same or different angles of incidence at the same or different times. The light sources may be configured according to any of the embodiments described herein. In addition one of the light sources may be configured according to any of the embodiments described herein, and another light source may be any other light source known in the art. In some embodiments, an inspection system may illuminate the wafer over more than one illumination area simultaneously. The multiple illumination areas may spatially overlap. The multiple illumination areas may be spatially distinct. In some embodiments, an inspection system may illuminate the wafer over more than one illumination area at different times. The different illumination areas may temporally overlap (i.e., simultaneously illuminated over some period of time). The different illumination areas may be temporally distinct. In general, the number of illumination areas may be arbitrary, and each illumination area may be of equal or different size, orientation, and angle of incidence. In yet another example, inspection system 100 may be a scanning spot system with one or more illumination areas that scan independently from any motion of wafer 123. In some embodiments an illumination area is made to scan in a repeated pattern along a scan line. The scan line may or may not align with the scan motion of wafer 123. Although as presented herein, wafer positioning system 125 generates motion of wafer 123 by coordinated rotational and translational movements, in yet another example, wafer positioning system 100 may generate motion of wafer 123 by coordinating two translational movements. For example motion wafer positioning system 125 may generate motion along two orthogonal, linear axes (e.g., X-Y motion). In such embodiments, scan pitch may be defined as a distance between adjacent translational scans along either motion axis. In such embodiments, an inspection system includes an illumination source and a wafer positioning system. The illumination source supplies an amount of radiation to a surface of a wafer over an illumination area. The wafer positioning system moves the wafer in a scanning motion characterized by a scan pitch (e.g., scanning back and forth in one direction and stepping by an amount equal to the scan pitch in the orthogonal direction).

Accordingly, various modifications, adaptations, and combinations of various features of the described embodiments can be practiced without departing from the scope of the invention as set forth in the claims.

What is claimed is:
1. An inspection system comprising:
 an illumination source configured to generate a beam of illumination light directed to a surface of a specimen;
 one or more optical elements configured to collect an amount of light from each pixel of an inspection area of the surface of the specimen illuminated by the illumination source;
 a first array of photodetectors including a first plurality of avalanche photodiodes operable in a Geiger mode, the first array of photodetectors having a first imaging resolution, wherein the first array of photodetectors is operable to receive a first portion of each amount of light collected from each pixel of the inspection area and generate a first plurality of output values based on the received first portion of each amount of collected light; and a second array of photodetectors having a second imaging resolution, the second array of photodetectors operable to receive a second portion of each amount of light collected from each pixel of the inspection area and generate a second plurality of output values based on the received second portion of each amount of collected light.

2. The inspection system of claim 1, further comprising:
 a beam splitter operable to receive the amount of light collected from each pixel of the inspection area and direct the first portion of each amount of collected light to the first array of photodetectors and direct the second portion of each amount of collected light to the second array of photodetectors.

3. The inspection system of claim 1, wherein the second portion of each amount of collected light is reflected from a surface of the first array of photodetectors toward the second array of photodetectors.

4. The inspection system of claim 1, wherein the first array of photodetectors and the second array of photodetectors are interleaved within an integrated detector.

5. The inspection system of claim 1, wherein the first array of photodetectors and the second array of photodetectors are arranged in a stacked configuration such that the second portion of each amount of collected light passes through the first array of photodetectors to reach the second array of photodetectors.

6. The inspection system of claim 1, wherein the second array of photodetectors includes a second plurality of avalanche photodiodes operable in a linear mode.

7. The inspection system of claim 6, wherein the first array of photodetectors includes a third plurality of avalanche photodiodes operable in a linear mode and the second array of photodetectors includes a fourth plurality of avalanche photodiodes operable in a Geiger mode.

8. The inspection system of claim 1, further comprising:
 drive electronics configured to switch the first plurality of avalanche photodiodes between a Geiger mode of operation and a linear mode of operation.

9. The inspection system of claim 8, wherein the drive electronics switch the first plurality of avalanche photodiodes between a Geiger mode of operation and a linear mode of operation at a switching frequency.

10. The inspection system of claim 1, further comprising:
 a microlens array disposed in front of the first array of photodetectors to focus the first portion of each amount of light collected from each pixel of the inspection area onto the first array of photodetectors.

11. The inspection system of claim 1, wherein the first and second plurality of avalanche photodiodes are either front illuminated avalanche photodiodes or back-thinned avalanche photodiodes.

12. A method comprising:
 generating a beam of illumination light directed to a surface of a specimen;
 collecting an amount of light from each pixel of an inspection area of the surface of the specimen illuminated by the illumination light;
 receiving a first portion of each amount of light collected from each pixel of the inspection area onto a first array of photodetectors including a first plurality of avalanche photodiodes operable in a Geiger mode, the first array of photodetectors having a first imaging resolution;
 generating a first plurality of output values based on the received first portion of each amount of collected light;
 receiving a second portion of each amount of light collected from each pixel of the inspection area onto a second array of photodetectors, the second array of photodetectors having a second imaging resolution; and generating a second plurality of output values based on the received second portion of each amount of collected light.

13. The method of claim 12, further comprising:

dividing the amount of light collected from each pixel of the inspection area into the first portion of each amount of collected light directed to the first array of photodetectors and the second portion of each amount of collected light directed to the second array of photodetectors.

14. The method of claim 12, further comprising:

reflecting the second portion of each amount of collected light from a surface of the first array of photodetectors toward the second array of photodetectors.

15. The method of claim 12, wherein the first array of photodetectors and the second array of photodetectors are interleaved within an integrated detector.

16. The method of claim 12, further comprising:

transmitting the second portion of each amount of collected light through the first array of photodetectors to reach the second array of photodetectors, wherein the first array of photodetectors and the second array of photodetectors are arranged in a stacked configuration.

17. The method of claim 12, wherein the second array of photodetectors includes a second plurality of avalanche photodiodes operable in a linear mode.

18. The method of claim 12, further comprising:

switching the first plurality of avalanche photodiodes between a Geiger mode of operation and a linear mode of operation.

19. An optical detector comprising:

a first array of photodetectors including a first plurality of avalanche photodiodes operable in a Geiger mode, the first array of photodetectors having a first imaging resolution, wherein the first array of photodetectors is operable to receive a first portion of each amount of light collected from each pixel of an inspection area and generate a first plurality of output values based on the received first portion of each amount of collected light; and a second array of photodetectors including a second plurality of photodiodes operable in a linear mode, the second array of photodetectors having a second imaging resolution, wherein the second array of photodetectors is operable to receive a second portion of each amount of light collected from each pixel of the inspection area and generate a second plurality of output values based on the received second portion of each amount of collected light.

20. The optical detector of claim 19, further comprising:

drive electronics configured to switch the first plurality of avalanche photodiodes between a Geiger mode of operation and a linear mode of operation.

* * * * *